United States Patent
He et al.

(10) Patent No.: US 7,433,737 B2
(45) Date of Patent: Oct. 7, 2008

(54) IMPLANTABLE MEDICAL DEVICE WITH POLYMER-POLYMER INTERFACES AND METHODS OF MANUFACTURE AND USE

(75) Inventors: Tom Xiaohai He, Simi Valley, CA (US); Matthew Isaac Haller, Valley Village, CA (US); Meredith Lee Anderson, Newhall, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 409 days.

(21) Appl. No.: 11/125,780

(22) Filed: May 10, 2005

(65) Prior Publication Data

US 2006/0259090 A1    Nov. 16, 2006

(51) Int. Cl.
*A61N 1/375* (2006.01)
*B32B 37/00* (2006.01)
*B23K 26/00* (2006.01)

(52) U.S. Cl. .................. 607/36; 607/37; 156/272.8; 219/121.64

(58) Field of Classification Search ............ 607/36, 607/37; 174/50.5, 50.58; 53/477; 220/521; 228/124.6
See application file for complete search history.

(56) References Cited

U.S. PATENT DOCUMENTS

| | | | |
|---|---|---|---|
| 3,718,142 A | 2/1973 | Mulier | |
| 3,842,842 A * | 10/1974 | Kenny et al. | 607/36 |
| 5,193,539 A | 3/1993 | Schulman et al. | |
| 5,193,540 A | 3/1993 | Schulman et al. | |
| 5,312,439 A | 5/1994 | Loeb | |
| 5,674,259 A * | 10/1997 | Gray | 607/20 |
| 5,895,980 A * | 4/1999 | Thompson | 607/36 |
| 6,051,017 A | 4/2000 | Loeb et al. | |
| 6,960,111 B2 * | 11/2005 | Takegami et al. | 445/24 |
| 7,175,980 B2 * | 2/2007 | Qiu et al. | 435/4 |
| 2003/0073936 A1 * | 4/2003 | Raisanen | 600/595 |
| 2003/0114769 A1 * | 6/2003 | Loeb et al. | 600/513 |
| 2004/0059392 A1 | 3/2004 | Parramon et al. | |

FOREIGN PATENT DOCUMENTS

| | | |
|---|---|---|
| WO | WO 98/37926 | 9/1998 |
| WO | WO 98/43700 | 10/1998 |
| WO | WO 98/43701 | 10/1998 |

\* cited by examiner

*Primary Examiner*—Carl H. Layno
*Assistant Examiner*—Natasha N Patel
(74) *Attorney, Agent, or Firm*—Darby & Darby, P.C.; Bruce E. Black

(57) ABSTRACT

An implantable stimulator that includes a housing, a first plastic component, and a second plastic component, where the first and second plastic components form a polymer-polymer interface. A light absorbing metal layer is disposed over at least a portion of the interface and an electronic subassembly is disposed within the housing. The first and second plastic components can be welded together by irradiating the light absorbing metal layer which converts the light to heat.

11 Claims, 4 Drawing Sheets

IMPLANTABLE MEDICAL DEVICE WITH POLYMER-POLYMER INTERFACES AND METHODS OF MANUFACTURE AND USE

FIELD

The invention is directed to implantable medical devices, such as implantable stimulators, and methods of making and using the devices.

BACKGROUND

Implantable medical devices have been used effectively to treat many medical conditions and disorders. For example, implantable stimulators can be used in neurological therapy by stimulating nerves or muscles, for example, stimulating the spinal cord or other nerves for treatment of pain; for urinary urge incontinence by stimulating nerve fibers proximal to the pudendal nerves of the pelvic floor; for erectile and other sexual dysfunctions by stimulating the cavernous nerve(s); for reduction of pressure sores or venous stasis; etc.

Implantable stimulators typically include a housing that contains the electronic circuitry and a power source that produces electrical pulses at exposed electrodes, which may be connected to the housing via a lead, for stimulation of the tissue. It is preferable that the electronic circuitry and power source be held within the housing in a hermetically-sealed environment for the protection of the user and the protection of the circuitry and power source. It can be convenient or economical to form the housing and other portions of the exterior of the stimulator (or other medical device) out of plastic materials. Interfaces between these materials must be sealed to form the hermetic environment within the housing. Sealing a polymer-polymer interface can be time-consuming and many methods for sealing may include or produce materials that are potentially not biocompatible or may require a regulatory approval process to permit their use in sealing the housing.

BRIEF SUMMARY

One embodiment is an implantable stimulator that includes a housing, a first plastic component, and a second plastic component, where the first and second plastic components form a polymer-polymer interface. A light absorbing metal layer is disposed over at least a portion of the interface and an electronic subassembly is disposed within the housing.

Another embodiment is a method of making an implantable stimulator. A polymer-polymer interface is formed between two portions of the implantable stimulator. A light absorbing metal layer is disposed on the interface. The light absorbing metal layer is irradiated with a laser to heat the metal layer and weld the interface.

Yet another embodiment is an implantable stimulator that includes a housing and an electronic subassembly disposed within the housing. The housing forms a polymer-polymer interface and the interface is welded by irradiating a light absorbing metal layer disposed over the interface with a laser.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

DETAILED DESCRIPTION

Figure 1:
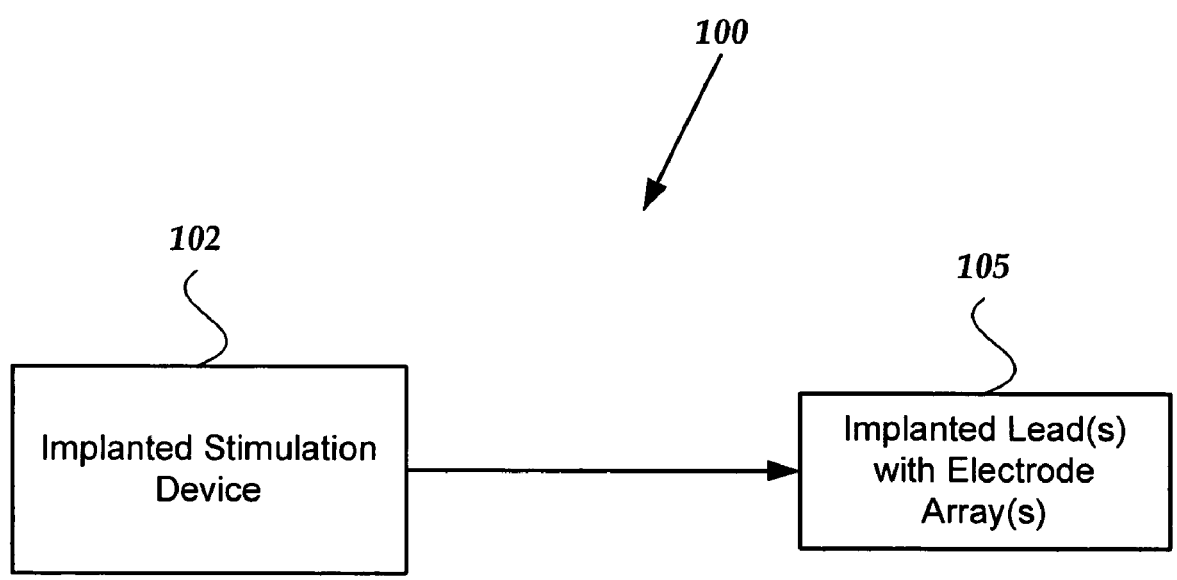
FIG. 1 is a schematic view of one embodiment of an implantable stimulator, according to the invention.

The invention is directed to implantable medical devices, such as implantable stimulators, with polymer-polymer interfaces and methods of making and using the devices.

An implantable medical device, such as an implantable stimulator, can be formed using one or more plastic components, such as a plastic housing, conductive plastic electrode(s), plastic electrode(s) with conductive material disposed over at least a portion of the plastic electrode(s), or other external components. The housing (or any other component) is optionally formed as one or more plastic pieces that are sealed together during manufacture. In at least some embodiments, the implantable medical device with one or more plastic components can be easier or less costly to manufacture than those manufactured with comparable metal or ceramic component(s), or there can be a reduction in the time, manpower, or skill used to manufacture the device. In addition, the plastic component(s) may be more permeable to RF signals than metal or ceramic. These RF signals can be used to charge a battery in the housing or to provide data or instructions to a processor disposed in the housing.

There are a number of methods for coupling plastic components together. For an implantable medical device, the coupling of these components preferably forms a hermetic seal. One method for joining polymer-polymer interfaces is laser welding which can provide a clean and precise method for forming a hermetic seal at a polymer-polymer interface.

An infrared or visible laser (for example, a near infrared laser) can be used to perform laser welding; however, polymers often do not absorb sufficient infrared or visible light by themselves to efficiently weld these interfaces. It will be recognized that other lasers, such as ultraviolet lasers, could be used as well. Often infrared lasers are preferred because materials that are transparent or translucent to visible light can be used in the welding process.

In some applications, infrared or visible light absorbing particles, such as pigments or dyes, are added to the polymer to allow welding at the interface. The use of such particles in implantable devices, however, may require further governmental approval (e.g., approval from the U.S. FDA) and/or substantial clinical testing to demonstrate that the device is biocompatible and safe for implantation.

Other infrared or visible absorbing compounds, such as CLEARWELD™ (Gentex Corporation, Simpson, Pa.), can be used to laser weld polymer interfaces. These materials, however, can be difficult to apply, labor-intensive, difficult to maintain cleanliness of the device and/or surroundings, or difficult to maintain consistency and uniformity.

An alternative is the use of a light absorbing metal layer disposed on or near the laser weld site. This metal layer is capable of absorbing the selected laser light. For example, the metal layer can be an infrared absorbing metal layer or a visible light absorbing metal layer. The metal layer can be selected from metals already approved for use in implantable devices, such as, for example, gold or titanium. The metal layer can then absorb the radiation from the laser and convert that radiation into heat for laser welding the polymer-polymer interface. This method of laser welding can also be used for other implantable devices, such as implantable stimulators, as well as for other devices and applications. While not wishing to be bound by any theory, it is believed that heating the plastic using the laser and light absorbing metal layer results in the plastic bonding to the metal layer or other plastic layer or both.

Figure 2:
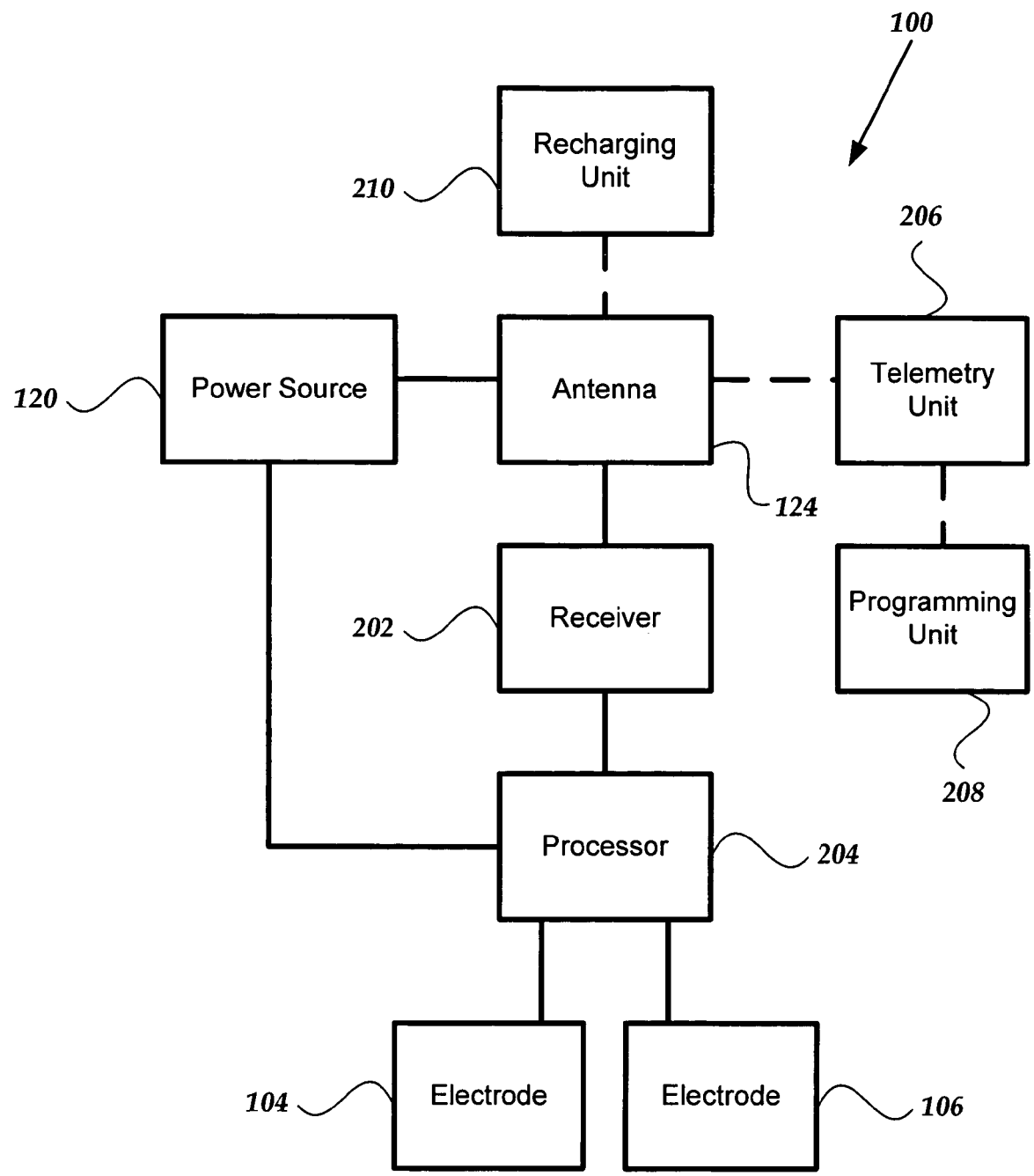
FIG. 2 is a schematic overview of components for a system for stimulation of body tissues, according to the invention.

The invention will be described using an implantable stimulator as an example. FIGS. 1 and 2 illustrate embodiments of implantable stimulator systems 100. The implantable stimulator system 100 includes an implantable stimulator unit 102 and an implantable lead 105 with an electrode array 103 that includes at least two electrodes 104, 106. The implantable stimulator unit 102 typically includes a power source 120, an electronic subassembly 122 (see FIG. 3), and an optional antenna 124. The implantable stimulator unit 102 provides signals to the electrodes 104, 106 to stimulate the desired tissue. The components of the implantable stimulator unit 102 are typically provided in a housing 140 (see FIG. 3.) Other embodiments of an implantable stimulator unit may include more or fewer components. It will be understood that the power source 120 and/or components of the electronic subassembly 122 and/or the optional antenna 124 can be provided outside of the housing 140 in a separate unit and coupled to the implantable stimulator unit 102 by a lead.

Figure 3:
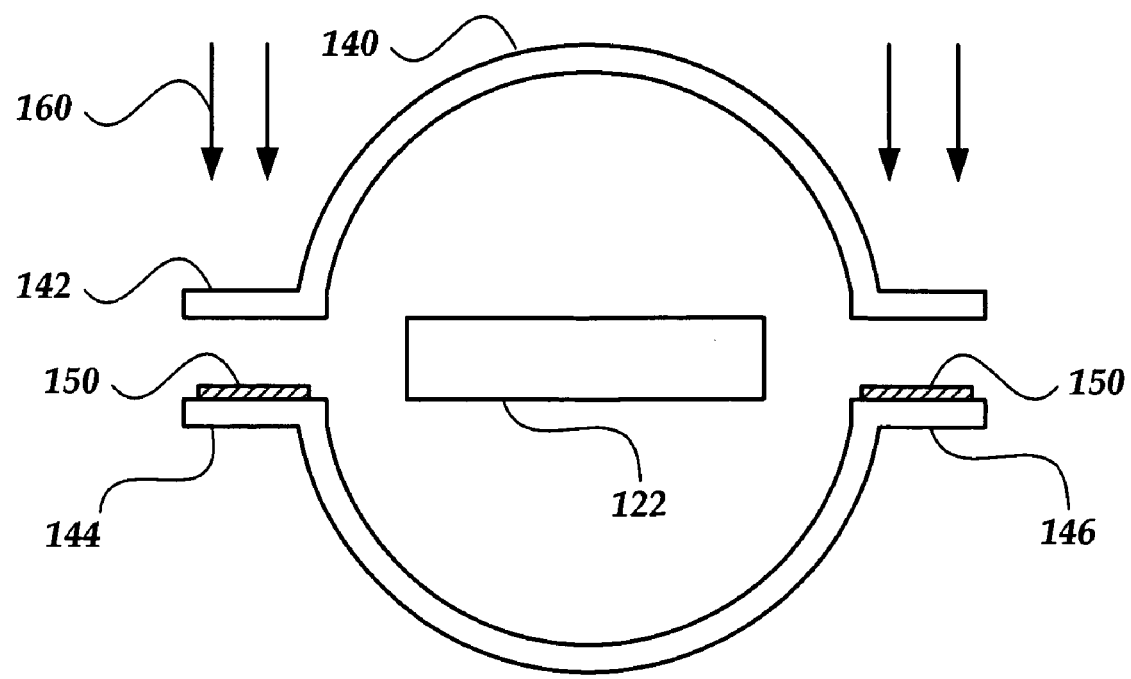
FIG. 3 is a schematic cross-sectional view of one embodiment of a method of laser welding two components of a housing together, according to the invention.

FIG. 3 illustrates a cross-sectional view of one embodiment of a housing 140 of an implantable stimulator unit 102. The housing includes two portions 142, 144 that are brought together to form a hermetically-sealed environment for the electrical components of the implantable stimulator unit. The two portions 142, 144 can be separate portions or these portions can be coupled together, prior to sealing, by a hinge or the like. The coupling of the two portions of the housing together using laser welding is one example of the invention. It will be understood that the invention can be used to couple any two plastic portions of the stimulator (or other device) together.

In this embodiment, the housing is formed of a plastic material. Preferably, the material of any plastic component is a hydrophobic polymer material. The plastic material can be a homopolymer, a copolymer formed using two or more different monomeric units, or a mixture of polymers or other materials. Examples of suitable polymer materials include polyolefins, polypropylene homopolymers and copolymers, teflon, and polyetheretherketone (PEEK). The plastic component may also include additives such as, for example, fillers, plasticizers, antioxidants, colorants, and the like.

The thickness of the walls of a plastic housing may impact the moisture permeability of the plastic housing. A minimum thickness needed to achieve a particular degree of resistance to moisture transport will often depend on the material selected for the housing, as well as any additives. In general, however, the thickness of the walls of the plastic housing is at least 100 µm and typically ranges from 50 to 10,000 µm. The housing 140 can have any shape including, for example, clam-shell (as illustrated in FIG. 3), cylindrical, conical, parallelepiped, cubic, and the like.

The portions 142, 144 of the housing 140 are preferably coupled together to form a hermetically-sealed environment within the housing. Laser welding can be used to couple any plastic component(s), or portions of plastic component(s), together at a polymer-polymer interface. To perform the laser welding, a light absorbing metal layer 150 (for example, an infrared absorbing metal) is disposed over at least a portion of the polymer-polymer interface between the first and second plastic portions 142, 144. For example, the metal layer 150 can be disposed on a flange 146 or rim of the portion 144. For an implantable medical device, such as the implantable stimulator, the light absorbing metal layer 150 is preferably a metal that is acceptable for use in implantable devices. Such metals include, but are not limited to, gold, titanium, platinum, and iridium, among others.

Figure 4:
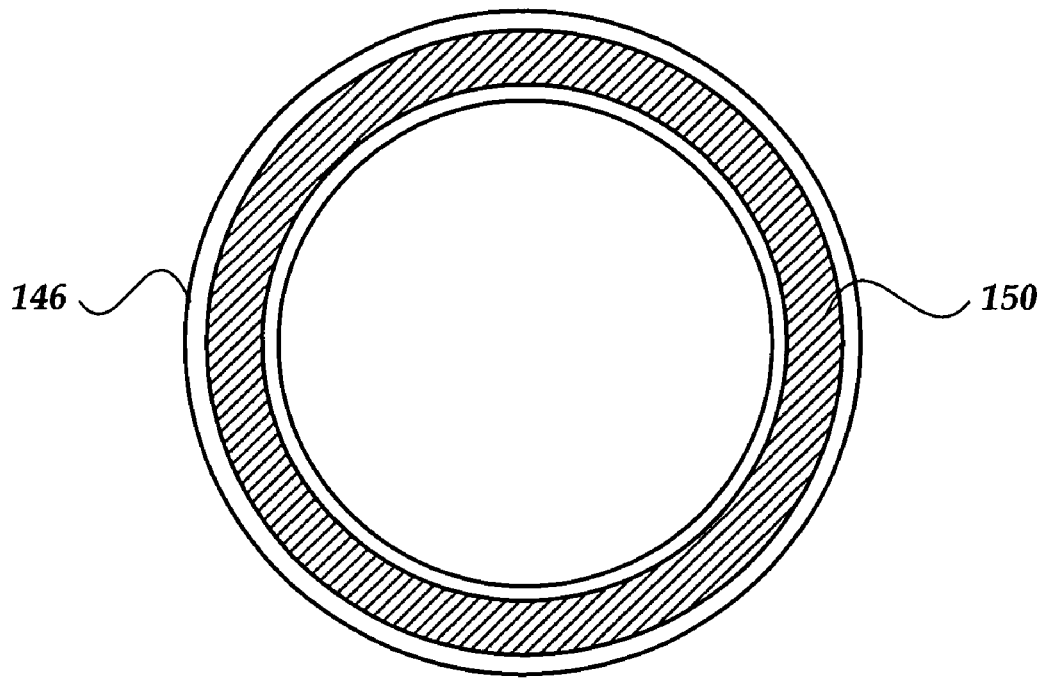
FIG. 4 is a schematic top view of one embodiment of one portion of the housing of FIG. 3 with a metal layer disposed on a rim of the housing, according to the invention.
Figure 5:
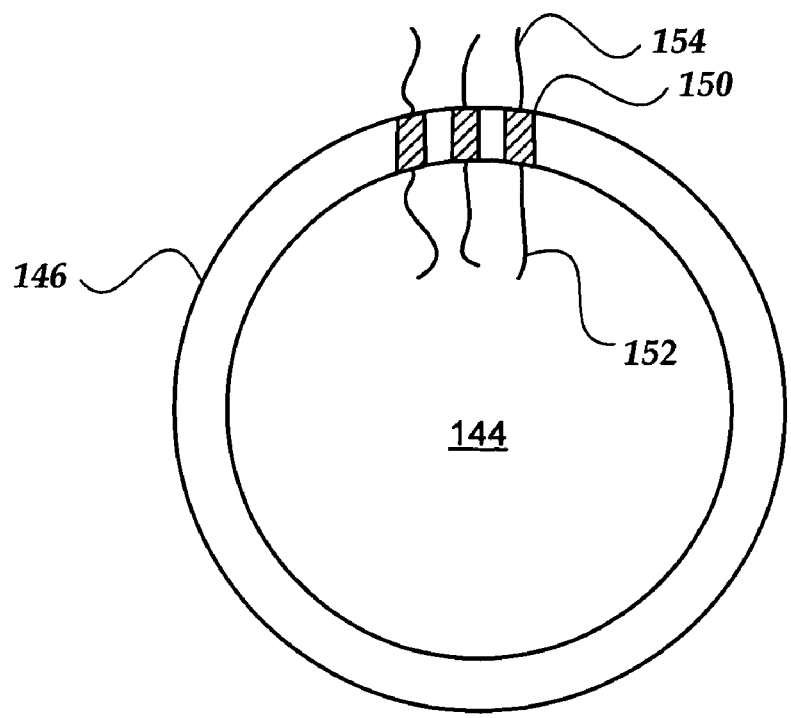
FIG. 5 is a schematic top view of one embodiment of another portion of the housing of FIG. 3 with a metal layer disposed on a rim of the housing, according to the invention.
Figure 6:
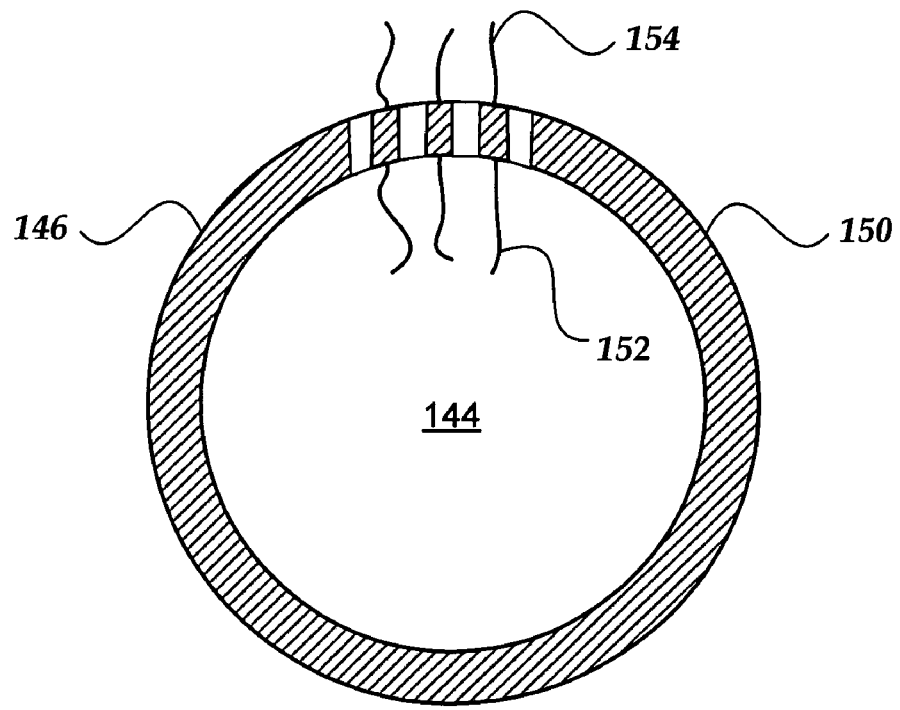
FIG. 6 is a schematic top view of one embodiment of yet another portion of the housing of FIG. 3 with a metal layer disposed on a rim of the housing, according to the invention.

The metal layer 150 can be disposed using any suitable technique including, but not limited, to physical or chemical vapor deposition, sputtering, coating, electroplating, and electroless plating. The metal layer may be disposed over an entire portion of the interface, as illustrated in FIG. 4, or can be patterned, as illustrated in FIG. 5, to thereby provide a conductive feedthrough. Patterning of the metal layer can occur during deposition of the metal layer or afterwards by, for example, etching a portion of the deposited metal layer. Patterning of the metal layer 150 can be particularly useful when the metal is used as a portion of the electrode or as another electrically active component or as a contact from the interior of the housing to an external electrode or lead, as illustrated in FIG. 5. For example, the portions of the patterned metal layer 150 can be coupled to internal electrical components using conductors 152 and coupled to external electrical components using conductors 154. FIG. 6 illustrates yet another patterned embodiment in which only a portion of the patterned metal layer (the feedthrough portion) is used to carry electrical signals.

It will be recognized that the implantable stimulator can include two or more polymer-polymer interfaces and a light absorbing metal layer can be formed for each interface, if desired. In some embodiments, a single metal layer may extend over portions (or all) of two or more polymer-polymer interfaces and can be used to couple each of those interfaces together. Laser welding of multiple interfaces may occur simultaneously or sequentially.

In the laser welding process, the metal layer 150, or a portion of the metal layer, is targeted using a laser (e.g., an infrared laser or a visible laser). The metal layer absorbs the laser radiation 160 and converts the radiation into heat which will then heat the adjacent plastic materials of the portions 142, 144 and seal the polymer-polymer interface. Optionally, if the metal layer 150 is patterned (or even if it is not patterned), a non-conducting, light-absorbing material, such as CLEARWELD™, can be coated over at least a portion of the polymer-polymer interface (particularly, the portion that is not in contact with the metal layer) to further facilitate laser welding the plastic materials together.

A power source 120 can be disposed within the housing 140. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the implantable stimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 2) external to the user.

In one embodiment, electrical current is emitted by the electrodes 104, 106 to simulate motor nerve fibers, muscle fibers, or other body tissues. The electronic subassembly 122 provides the electronics used to operate the implantable stimulator and generate the electrical pulses at the electrodes 104, 106 to produce stimulation of the body tissues. FIG. 2 illustrates one embodiment of components of the electronic subassembly and associated units. It will be understood that the electronic subassembly can include more, fewer, or different components and can have a variety of different configurations. Some or all of the components of the electronic subassembly can be positioned on one or more circuit boards or similar carriers within the housing, if desired.

In the illustrated embodiment, a processor 204 is provided to control the timing and electrical characteristics of the implantable stimulator. For example, the processor can, if desired, control one or more of the timing, periodicity, strength, duration, and waveform of the pulses. Any processor can be used and can be as simple as a electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the implantable stimulator. For example, the signals may be used to modify the pulses of the implantable stimulator such as modifying one or more of pulse duration, pulse frequency, pulse waveform, and pulse strength. The signals may also direct the implantable stimulator to cease operation or to start operation or to start charging the battery.

Optionally, the implantable stimulator may include a transmitter (not shown) coupled to the processor and antenna for transmitting signals back to the telemetry unit 206 or another unit capable of receiving the signals. For example, the implantable stimulator may transmit signals indicating whether the implantable stimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the plastic housing.

The implantable stimulator can be implanted into the body tissue using a variety of methods including surgical methods.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making an implantable stimulator, the method comprising:

forming a polymer-polymer interface between two portions of the implantable stimulator, each portion of the implantable stimulator comprising a polymeric component;

disposing a light absorbing metal layer on the interface; and irradiating the light absorbing metal layer with a laser to heat the metal layer to weld the interface forming a direct polymer-to-polymer bond between the two portions of the implantable stimulator, wherein the direct polymer-to-polymer bond comprises a region in which the polymeric components of the two portions of the implantable stimulator are in direct contact with each other and directly bonded without the light absorbing metal layer between the polymeric components.

2. The method of claim 1, wherein the light absorbing metal layer is an infrared absorbing metal layer and the laser is an infrared laser.

3. The method of claim 1, wherein forming a polymer-polymer interface comprises forming a polymer-polymer interface between two portions of a housing of the implantable stimulator.

4. The method of claim 1, further comprising forming a second polymer-polymer interface that is non-contiguous with the polymer-polymer interface.

5. The method of claim 4, further comprising disposing a second light absorbing metal layer on the interface, and irradiating the second light absorbing metal layer with a laser to heat the metal and weld the second interface.

6. The method of claim 1, wherein disposing a light absorbing metal layer on the interface comprises patterning the metal layer on the interface.

7. The method of claim 1, further comprising disposing an electronic subassembly in a housing of the implantable stimulator.

8. The method of claim 7, further comprising coupling the metal layer to the electronic subassembly and to at least one electrode external to the housing, wherein the metal layer provides a conduit for transmission of stimulation signals generated by the electronic assembly to the at least one electrode external to the housing.

9. The method of claim 8, further comprising disposing a non-conductive light absorbing material over at least some portion of the interface not in contact with the metal layer.

10. The method of claim 7, further comprising coupling at least one electrode to a housing of the implantable stimulator.

11. The method of claim 10, wherein coupling at least one electrode to the housing comprises coupling at least one electrode to the metal layer and to the electronic subassembly, wherein the metal layer is patterned, and provides a conduit for transmission of stimulation signals generated by the electronic assembly to the at least one electrode.

* * * * *